(12) United States Patent
Wegener et al.

(10) Patent No.: US 8,124,141 B2
(45) Date of Patent: Feb. 28, 2012

(54) RAPIDLY ABSORBING LIPOPHILIC SKIN COMPOSITIONS AND USES THEREFOR

(75) Inventors: Paul T. Wegener, New York, NY (US); Yukihiko Hara, Tokyo (JP)

(73) Assignees: Mitsui Norin Co., Ltd., Tokyo (JP); Epitome Pharmaceuticals Limited, Halifax, Noca Scotia ( * ) Notice: Subject to any disclaimer, the term of this patent is extended or adjusted under 35 U.S.C. 154(b) by 796 days.

(21) Appl. No.: 10/548,851

(22) PCT Filed: Mar. 4, 2004

(86) PCT No.: PCT/US2004/006929
§ 371 (c)(1),
(2), (4) Date: Jun. 14, 2006

(87) PCT Pub. No.: WO2004/080399
PCT Pub. Date: Sep. 23, 2004

(65) Prior Publication Data
US 2006/0275509 A1    Dec. 7, 2006

Related U.S. Application Data

(60) Provisional application No. 60/454,287, filed on Mar. 12, 2003.

(51) Int. Cl.
*A61K 36/82* (2006.01)
(52) U.S. Cl. ............ 424/729; 424/725; 424/401
(58) Field of Classification Search .......... None
See application file for complete search history.

(56) References Cited

U.S. PATENT DOCUMENTS

| | | | |
|---|---|---|---|
| 4,892,890 A | 1/1990 | Damani | |
| 5,211,944 A * | 5/1993 | Tempesta | 424/78.08 |
| 5,827,886 A * | 10/1998 | Hersh | 514/562 |
| 6,187,938 B1 | 2/2001 | Hrabalek et al. | |
| 6,248,346 B1 | 6/2001 | Hara et al. | |
| 6,541,042 B1 | 4/2003 | Frater-Schroder et al. | |
| 6,589,514 B2 * | 7/2003 | Jensen et al. | 424/59 |
| 6,723,732 B1 | 4/2004 | Sugita et al. | |
| 6,960,360 B2 * | 11/2005 | Gourdin et al. | 424/732 |
| 7,169,400 B2 * | 1/2007 | Luu et al. | 424/400 |
| 7,175,987 B2 * | 2/2007 | Rosenbloom | 435/6 |
| 2001/0001666 A1 | 5/2001 | Harbeck | |
| 2003/0224072 A1 * | 12/2003 | Frome | 424/736 |
| 2009/0092576 A1 * | 4/2009 | Trimble | 424/78.07 |

FOREIGN PATENT DOCUMENTS

| | | |
|---|---|---|
| EP | 581587 | 7/1993 |
| EP | 0657169 | 6/1995 |
| EP | 569338 | 8/1998 |
| EP | 1095660 | 10/2000 |
| EP | 0947193 | 5/2005 |
| JP | 61024511 | 2/1986 |
| JP | 1186824 | 7/1989 |
| JP | 4149135 | 5/1992 |
| JP | 6239716 | 8/1994 |
| JP | 109229 A | 1/1998 |
| JP | 10257856 | 9/1998 |
| JP | 11315016 | 11/1999 |
| JP | 2000103714 | 4/2000 |
| JP | 2002047196 | 2/2002 |
| JP | 2002121152 | 4/2002 |
| JP | 2002533365 | 10/2002 |
| JP | 4074138 B2 | 4/2008 |
| WO | WO 93/23019 | 11/1993 |
| WO | WO 93/23025 | 11/1993 |
| WO | WO 96/03131 | 8/1996 |
| WO | WO 97/06788 | 2/1997 |
| WO | 9904764 | 2/1999 |
| WO | 0029021 A1 | 5/2000 |
| WO | W00038625 | 7/2000 |
| WO | 0128491 A2 | 4/2001 |
| WO | WO02072047 | 9/2002 |

OTHER PUBLICATIONS http://www.webmd.com/skin-problems-and-treatments/tc/cold-sores-topic-overview?page=2—accessed May 2009.*
Cheng, H., et al, "Antiviral properties of prodelphinidin B-2 3'O-gallate from green tea leaf", Antiviral Chemistry & Chemotherapy, vol. 13, pp. 223-229. 2002.

* cited by examiner

*Primary Examiner* — Susan Hoffman
(74) *Attorney, Agent, or Firm* — Fish & Associates, PC

(57) ABSTRACT

Topical compositions, and particularly hydrophobic compositions include an essential oil in an amount effective to achieve substantially complete absorption of the composition in the skin without leaving a greasy residue. Especially preferred topical compositions may also include pharmaceutically active agents (e.g., polyphenol), additional essential oils, stabilizers, etc. In further preferred aspects, contemplated compositions may delay onset, or even prevent viral eruptions on the skin, and where applied as a lipstick, will increase reddening of the lip as well as reduce chapping.

12 Claims, No Drawings

RAPIDLY ABSORBING LIPOPHILIC SKIN COMPOSITIONS AND USES THEREFOR

This application claims the benefit of U.S. provisional patent application with the Ser. No. 60/454,287, which was filed Mar. 12, 2003, and which is incorporated by reference herein.

FIELD OF THE INVENTION

Cosmetic and pharmaceutical topical compositions, and particularly lipophilic topical compositions.

BACKGROUND OF THE INVENTION

Numerous pharmacologically active ingredients are unstable in the presence of water. Thus, where such ingredients are topically applied to the skin, delivery will typically require use of a hydrophobic vehicle. Unfortunately, hydrophobic vehicles generally absorb poorly into the skin and often lack a desirable look and feel.

For example, while some sunscreen formulations will remain almost completely on the surface of the skin to provide protection against UV irradiation, they will often give a greasy look or feel to a user. In another example, various lip stick or lip balm formulations will be partly absorbed to provide both, a soft feel to the lip as well as the desired coloring on the surface of the lip. However, most of these formulations will only poorly adhere to the lip and are typically formulated to provide a residual lipophilic coat on the lip. Where a pharmaceutically active agent is to be delivered into the skin from a hydrophobic vehicle, skin penetration enhancers may be included into such formulations to enhance delivery.

Exemplary penetration enhancers, compositions including same, and methods of use are described in WO 93/23019, WO 93/23025, EP 569338, EP 581587, WO 96/03131, or WO 97/06788. Most of the known penetration enhancers provide a significant improvement in delivery of a specific pharmaceutically active molecule through skin. However, the effect of such enhancers on the absorption of the entire preparation is often less than desirable in hydrophobic preparations. Therefore, even if the penetration enhancer increases flux of a pharmaceutically active molecule through the skin, the vehicle typically remains on the skin in relatively high quantities.

To circumvent at least some of the problems associated with remaining vehicle on the skin, various approaches shave been taken. For example, uptake of a hydrophobic vehicle may be forced using occlusive topical administration in which the vehicle is continuously presented to the skin (e.g., under of a film forming polymer or preformed barrier material). Occlusion generally tends to increase uptake of hydrophobic compositions into the skin, however, has several disadvantages. Among other things, occlusive preparations often need to remain attached to the skin over a prolonged period of time, which tends to present problems associated with: low tolerance to such compositions. Moreover, occlusive preparations are generally limited to use on non-facial skin and are only rarely (if ever) used on lips.

In another approach, an additive may be provided to the topical formulation that increases uptake of the formulation (i.e., vehicle and the pharmaceutically active agent) as described by Hrabalek et al. in U.S. Pat. No. 6,187,938. Here, certain omega amino acid derivatives are used to enhance penetration of a hydrophobic vehicle through skin. Similarly, as described in U.S. Pat. No. 4,892,890 to Damani, propylene glycol is used to increase uptake of the hydrophobic analgesic formulation. While such formulations have generally increased vehicle uptake, various difficulties still remain. Among other things, stability of at least some of the omega amino acid derivatives may be less than desirable. Furthermore, not all of the omega amino acids may be tolerated well, especially over a prolonged period of administration. Similarly, while propylene glycol increases vehicle absorption where the vehicle comprises significant quantities of waxes, propylene glycol (and other polyhydroxy compounds) will not increase absorption of other known hydrophobic vehicles equally well.

Thus, although various compositions and methods are known in the art to provide hydrophobic compositions to the skin, all or almost all of them suffer from one or more disadvantage. Therefore, there is still a need to provide improved compositions and methods for delivery of hydrophobic compositions to the skin.

SUMMARY OF THE INVENTION

The present invention is directed to methods and compositions for pharmaceutical and cosmetic formulations (preferably comprising a pharmaceutically active agent) in which an essential oil is present at a amount effective to achieve substantially complete absorption of the topical formulation into the skin without leaving a greasy residue.

In especially preferred aspects of the inventive subject matter, the essential oil has analgesic properties, and/or is prepared from Pelargonium graveolens, while particularly preferred pharmaceutically active agents comprise a polyphenol (e.g., POLYPHENON E) at a concentration of at least 2 wt %. Furthermore, contemplated topical formulations may also include a stabilizer (e.g., ascorbic acid or an ascorbic acid derivative in an amount that is at least 20% of an equimolar quantity of the polyphenol), and/or a second essential oil, which may enhance the analgesic effect of the formulation, but itself has no analgesic effect. Such second essential oils especially include bergamot oil, eucalyptus oil, lavender oil, chamomile oil, and/or melaleuca oil. Contemplated topical formulations may be especially useful in delaying or even preventing a viral outbreak on skin of a person infected with a virus (e.g., herpes virus or pox virus).

In another aspect of the inventive subject matter, a lipstick formulation comprises a polyphenol and at least one essential oil, wherein the polyphenol and the essential oil are present in an amount effective to reduce chapping of a lip. In such formulations, preferred essential oils include geranium oil, bergamot oil, eucalyptus oil, lavender oil, chamomile oil, and melaleuca oil. Additionally, it is particularly preferred that the polyphenol is present in an amount of between 2 wt % and 20 wt %, and the essential oil is present in an amount of between 0.5 wt % and 15 wt %.

In a further aspect of the inventive subject matter, a lipstick formulation comprises a combination of a polyphenol and an essential oil, wherein the polyphenol and the essential oil are present in an amount effective to increase persistent reddening of a lip (i.e., increase of reddening over a period of at least three hours after application). With respect to the essential oils and polyphenol, the same considerations as provided above apply.

Various objects, features, aspects and advantages of the present invention will become more apparent from the following detailed description of preferred embodiments of the invention.

DETAILED DESCRIPTION

The inventors have surprisingly discovered that essential oils in sufficient quantity in a hydrophobic formulation will promote rapid and complete absorption of the formulation into the skin of a user applying the formulation to the skin.

Commonly, many essential oils are employed in the art as perfume ingredients or as aromatherapy agents, and the concentration of essential oils in most commercially available formulations is generally less than 0.05 wt % (e.g., in a typical lip balm formulation). Since essential oils and their constituent terpenes are known to exhibit an extremely bitter taste, the concentrations of essential oil is often kept below 0.05 wt % in cosmetic formulations, and especially in lip balms to achieve a tolerable sensory product.

Unexpectedly, the inventor has discovered that the lip balms and other hydrophobic formulations are most effectively absorbed (e.g., absorbed completely), when quantities of essential oils of greater than 0.5 wt % are included in such formulations. Remarkably, such lip balms and other hydrophobic topical formulations have an unpleasant, bitter, and astringent taste, but the taste does not linger as the entire balm is rapidly absorbed.

The term "topical hydrophobic formulation" as used herein refers to any cosmetic and pharmaceutical formulation that is applied onto a surface of the body (e.g., skin, lip, mucous membrane), wherein the formulation includes less than 10 wt % water, more typically less than 5 wt % water, and most typically less than 1 wt % water. Therefore, especially preferred topical hydrophobic formulations will include oil- and/or wax-based formulations. It should be noted that the terms "hydrophobic" and "lipophilic" are used interchangeably herein.

As further used herein, the term "essential oil" refers to a mixture of compounds that is isolated from a plant and comprises a plurality of hydrophobic constituents (e.g., various terpenes, alcohol esters, aldehydes, ketones, phenols etc., typically soluble in water less than 10 wt %). In most cases, essential oils are prepared by water steam distillation, maceration, expression, and/or solvent extraction of plant materials. In contrast, an individual synthetic compound, or a natural compound purified to homogeneity (e.g., synthetic or isolated citral, pinene, camphor, etc.) are not considered an essential oil under the scope of this definition.

As also used herein, the term "substantially complete absorption of the formulation" means that no more than 10 wt % of the formulation, and more typically no more than 5 wt % of the formulation remains on the surface of the skin after application of the formulation onto the skin in an ordinary amount (e.g., between about 5-25 mg/cm$^2$) and after massaging the formulation into the skin for 1 minute.

It should be noted that several references report essential oils as penetration enhancers for pharmaceutically active agents from water in vitro across a cell membrane. For example, Abdullah et al. teach that eucalyptus oil enhances delivery of 5-fluorouracil into a cell from aqueous growth medium 60-fold, while peppermint oil and turpentine oil enhance delivery of the same compound 46- and 28-fold, respectively. However, it should be appreciated that the solubility of the essential oils in water limits the concentration to about 1 mg/ml, or less or equal than 0.1% (w/vol). Moreover, only 5-FU influx was increased, but not influx of the growth medium (which would correspond to the vehicle). Finally, such references employ a hydrophilic base (i.e., the growth medium) as the vehicle, but not a hydrophobic topical formulation.

In one preferred aspect of the inventive subject matter, suitable hydrophobic topical compositions may be prepared from a wax and mineral oil (preferably semi-solid, saturated hydrocarbons, mainly of paraffinic nature and dermatologically acceptable) base, and may further include various wool fats, triglycerides, fatty acids, silicon oils, etc. Depending on the particular purpose, the exact composition for contemplated hydrophobic topical formulations may vary considerably, and all known hydrophobic formulations are considered suitable for use herein. For example, suitable formulations for application to skin and lips are described in "A Formulary of Cosmetic Preparations: Creams, Lotions and Milks" by Anthony L. Hunting (ISBN: 187022809X). Alternatively, in less preferred aspects of the inventive subject matter, the topical formulation may also be a hydrophilic composition (i.e., includes at least 2 wt %, more typically at least 5 wt %, and most typically at least 10 wt % water). Therefore, suitable formulations may also be creams, lotions, mousses, etc.

With respect to essential oils, it should be recognized that all known essential oils are contemplated suitable for use herein. However, in preferred aspects of the inventive subject matter, suitable essential oils are prepared from plant material of one or more plant species using isolation methods well know to those skilled in the art. For example, contemplated essential oils include geranium oil, bergamot oil, eucalyptus oil, lavender oil, chamomile oil, and/or melaleuca oil. Suitable essential oils may be prepared by various protocols and contemplated protocols include steam distillation, maceration, and solvent extraction of plant parts, and especially leaves and petals. So prepared essential oils may further be refined to increase the content of a specific constituent, or to reduce the concentration of one or more less desired constituent.

Contemplated essential oils may have next to their absorption enhancing effect one or more additional effects. For example, an essential oil that is prepared from *Pelargonium graveolens* has significant analgesic properties, while other essential oils lack such characteristics. On the other hand, the inventor also discovered that non-analgesic essential oils may increase the analgesic effect (e.g. accelerated analgesic effect, greater pain relief, extended pain relief, and/or improved palatability) of *Pelargonium graveolens* essential oils. Such enhancing essential oils include bergamot oil, eucalyptus oil, lavender oil, chamomile oil, and melaleuca oil.

Similarly, in a less preferred aspect, the essential oil may also be supplemented with one or more component, and particularly preferred components include volatile compounds that are commonly found in plants (e.g., terpenes and terpenoids, which may or may not be synthetic). Alternatively, it should also be recognized that a plurality of compounds may be blended to prepare a synthetic essential oil having a composition that is similar (e.g. with at least 30% identical constituents) to an essential oil prepared from a plant. Of course, it should be recognized that suitable essential oils may be prepared from a single source, or may be a mixture of at least two essential oils having a distinct source (e.g., from a first and second plant, or from a plant and synthetic). Moreover, it should be recognized that numerous essential oils are commercially available, and all of the commercially available essential oils are deemed suitable for use herein. Alternatively, in at least some topical hydrophobic formulations, the essential oil may be replaced by an isolated terpene or terpenoids.

Regardless of the particular nature of contemplated essential oils, it is preferred that the essential oil in the topical formulations is present in a concentration that is effective to achieve substantially complete absorption of the formulation into a skin without leaving a greasy residue. For numerous of contemplated formulations, such concentration is between about 0.5 wt % to about 5.0 wt %, and even higher (e.g. between about 5.0 wt % to about 10 wt %, or between about 10 wt % to about 15 wt % or more). For example, where relatively rapid absorption is desired (e.g., anti-chap lip stick formulation), essential oils may be present in an amount greater than 5 wt %. On the other hand, lower quantities of essential oils (e.g., between about 1.0 wt % to about 4.0 wt %, or between about 0.1 wt % to about 0.5 wt % or less) may be preferred where the formulation need not be rapidly absorbed.

With respect to contemplated pharmaceutically active agents, it should be appreciated that the particular nature of such agents is not limiting to the inventive subject matter, and numerous pharmaceutically active agents are considered suitable for use herein. For example, suitable agents include synthetic and isolated drugs such as various analgesics (e.g., benzocaine, lidocaine, opiates, etc.), antibacterial agents (e.g., beta-lactam antibiotics, tetracyclicn-type antibiotics, etc.), anti-inflammatory agents (e.g., steroids, NSAIDs), antifungal agents (e.g., various azoles, naftifine, etc.), antiviral agents (e.g. RTIs, NNRTIs, nucleoside analogs, etc.), antimetabolites (e.g., methotrexate, mercaptopurine, etc.), antineoplastic agents (e.g., cis-platinum, 5-FU, etc.), cytostatic agents (e.g., various rubicins, bendamustine, etc.), enzyme regulators and inhibitors (e.g., competitive inhibitors, transition state analogs, etc.), immunomodulators (e.g., interferons, ribavirin, etc.), nucleic acids (e.g., siRNA, viral DNA or RNA), polypeptides (e.g., recombinant factors, enzymes, etc.), vitamins (E, K, or D), and all reasonable combinations thereof.

Similarly, contemplated pharmaceutically active agents may also be of natural origin, and are most preferably prepared from a plant or plant extract. Especially contemplated active agents include those having one or more known beneficial properties when topically or systemically administered, and particularly preferred plant extracts and preparations include polyphenol extracts from green tea (e.g., POLYPHENON E), antioxidant extracts from various berries (e.g., blueberry extracts, etc.), phytoestrogen extracts from soy, anti-androgenic extracts (e.g., saw palmetto extracts) etc. Additionally contemplated pharmaceutically active agents may also provide protective or cosmetic effect and most preferably include UV absorbers, dyes, skin bleaching agents (e.g., hydroquinone, kojic acid, etc.), and so forth.

Therefore, in some exemplary topical formulations, it is contemplated that the pharmaceutically active agent exhibits or produces catecholamine activity (e.g. by addition or catecholamines and/or related compounds) and may be applied to improve muscle tone of facial muscles and therefore make the face look firmer. Exemplary catecholamines include adrenaline, norepinepherine, dopamine and their precursors, most preferably tyrosine and phenylalanine. Similarly, contemplated formulations may further comprise a neurotransmitter synthesis enhancer (e.g., dimethylaminoethanol, and other co-factors such as vitamin $B_6$, pantothenic acid, or calcium pantothenate), or damper (e.g., botulinus toxin).

The amount of pharmaceutically active agents in contemplated topical may vary considerably and it should be recognized that the particular amount of pharmaceutically active agents will predominantly depend on the desired agent and therapeutic purpose. However, it is generally contemplated that the pharmaceutically active agents will be present in an amount of between about 0.001 wt % (and even less) to up to 50 wt % (or more where appropriate). For example, where the formulation includes a highly active pharmaceutically active agent (e.g., botulinus toxin), the concentration of the agent maybe between 0.001 wt % and 0.1 wt %. In another example, where the pharmaceutically active agent comprises an UV filter or antineoplastic agent, the concentration of the agent may be between 0.1 wt % and 5 wt %. On the other hand, where the pharmaceutically active agent comprises a plant extract (e.g., polyphenol), the pharmaceutically active agent may be present in an amount of at least 2 wt %, and most typically in an amount of between 2 wt % and 20 wt %.

While addition of various pharmaceutically active agents to contemplated topical hydrophobic formulations is generally preferred, it should also be appreciated that the essential oils at contemplated concentrations may have a therapeutic effect in their own right. Therefore, addition of the pharmaceutically active agent is optional in at least some of the contemplated formulations.

With respect to application of contemplated formulations to the skin, it is generally contemplated that all known manners of application are suitable for use herein, and therefore include manually rubbing/massaging the formulation into the skin, as well as all known applications under occlusion, etc. Depending on the particular composition and use, it should further be recognized that the quantity of topical composition may vary substantially. For example, where the topical composition is applied onto lips, amounts of 0.05 $mg/cm^2$ to 1.0 $mg/cm^2$ are suitable for most applications. On the other hand, where the topical composition is applied onto a skin area with relatively high absorbency, amounts of 0.5 $mg/cm^2$ to 10 $mg/cm^2$ (and even more) are deemed appropriate.

Still further, it should be appreciated that in the case of compounds that are unstable in water-containing formulations (e.g., ascorbic acid, plant polyphenols, or precursors for neurotransmitters), contemplated hydrophobic formulations not only provide an alternative avenue of maintaining such unstable compounds, but also enable rapid absorption of the ointment and complete delivery of the active ingredients into the skin.

Thus, the inventors contemplate a topical hydrophobic formulation comprising an essential oil and a pharmaceutically active agent, wherein the essential oil is present at a concentration effective to achieve substantially complete absorption of the formulation into a skin without leaving a greasy residue. With respect to the essential oil, it is typically preferred that the essential oil has analgesic properties (and is preferably prepared from *Pelargonium graveolens*). Further especially preferred pharmaceutically active agents include a polyphenol, and particularly a green tea polyphenol (e.g., POLYPHENON E) at a concentration of at least 2 wt %.

It should be recognized that where the pharmaceutically active agent is prone to oxidation, an antioxidant may be added and especially preferred antioxidants include ascorbic acid and derivatives thereof Antioxidants are preferably present in sub-equimolar to equimolar amounts, and most preferably in an amount that is at least 20% of an equimolar quantity of the antioxidant. It should further be appreciated that stabilizing amounts of antioxidants, and especially of ascorbic acid and derivatives thereof may also stabilize the green tea polyphenols in vivo. Thus, preferred formulations include those in which the pharmaceutically active agent comprises a polyphenol at an amount of at least 2 wt %, wherein the essential oil is prepared from Pelargonium graveolens, and wherein the formulation further comprises a ascorbic acid or an ascorbic acid derivative. Optionally, such formulations may further include a second essential oil (e.g., bergamot oil, eucalyptus oil, lavender oil, chamomile oil, and/or melaleuca oil).

In one especially preferred aspect of the inventive subject matter, the inventor discovered that hydrophobic topical compositions according to the inventive subject matter may be employed to delay onset or prevent a viral eruption on a skin (e.g., precipitated by herpes virus or pox virus) when such compositions include at least one of a green tea extract and an essential oil at a concentration effective to delay onset or prevent a viral eruption on a skin. Typically, the essential oil in such compositions is present at a concentration of at least 0.5 wt %, wherein the essential oil is preferably prepared from *Pelargonium graveolens*. The green tea extract (preferably a polyphenol extract, most preferably POLYPHENON E) is typically present at a concentration of between 2 wt % and 20 wt %.

In still further preferred aspects, contemplated hydrophobic topical compositions may also be formulated as lipstick or lip balm, and exhibit as such formulations various desirable properties. Among other things, the inventor discovered that such formulations will reduce chapping of the lips, especially where the formulation includes a polyphenol and an essential oil. Especially preferred essential oils for contemplated lip balm and lipstick formulations include geranium oil, bergamot oil, eucalyptus oil, lavender oil, chamomile oil, and melaleuca oil, which are typically present in an amount of between 0.5 wt % and 15 wt %, whereas the polyphenol is preferably present in an amount of between 2 wt % and 20 wt %. The terms "lipstick formulation" and "lip balm formulation" are used interchangeably herein and refer to formulations that are applied onto a lip.

Further observed beneficial results of such lipstick and lip balm formulations include an increase in persistent reddening of a lip where such formulations are applied to the lip. Therefore, the inventor contemplates a lipstick or lip balm formulation that includes a combination of a polyphenol and an essential oil, wherein the polyphenol and the essential oil are present in an amount effective to increase persistent reddening of a lip. The term "increase persistent reddening of a lip" as used herein means that reddening of the lip can be observed up to at least 2 hours, more typically at least 3 hours, and most typically at least 4 hours after application of the formulation. It should be recognized that such reddening is not caused by increased pigment transfer into the lip. On the contrary, the inventors contemplate (while not wishing to be bound to a specific theory or hypothesis) that the increased persistence in reddening is due to an increase in blood circulation in the lip. Sufficient amounts of the polyphenol for increased persistent reddening is between 2 wt % and 20 wt %, while the essential oil is preferably present in an amount of between 0.5 wt % and 15 wt %.

Experiments

The following exemplary protocol for rapid delivery of lipophilic compositions and uses is provided as guidance to a person of ordinary skill in the art. However, it should be recognized that numerous modifications may be made without departing from the inventive concept presented herein.

Rapid Absorption of Exemplary Formulation

Test conditions: An ointment containing 50 wt % petroleum jelly, 20 wt % beeswax, 18 wt % lanolin and 12 wt % green tea extract was mixed and held at 60° C. Varying amounts of essential oils, a blend of geranium oil (one part), bergamot oil (one part), tea tree oil (one part), lavender oil (two parts), and eucalyptus oil (one part) were added and the mixture was poured into jars.

For absorption experiments, 250 mg of each ointment were weighed and rubbed with the finger tips on the inside of the forearm. The rubbing time until the skin felt dry was determined, and the area over which the ointment spread was measured. Interestingly, it was found that the area covered appeared to be inversely proportional to the amount of ointment absorbed per unit area. Similar experiments were performed on the lips, measuring time to complete absorption for a fixed area and the results were comparable. It should be especially noted that absorption measured refers to the entire lipophilic composition, and not just to a portion (e.g., active ingredient) thereof.

| ESSENTIAL OILS (wt %) | SPEED OF ABSORPTION | AREA |
| --- | --- | --- |
| 0% | Not absorbed | Keeps spreading |
| 0.5% | 60 secs | 25 cm$^2$ per 250 mg |
| 2.0% | 15 secs | 10 cm$^2$ per 250 mg |
| 10.0% | 6 secs | 6 cm$^2$ per 250 mg |

Thus, it should be recognized that in contemplated compositions it is the quantity of the terpenes (e.g., essential oil or oil mixture) present in the lipophilic composition that determines the speed with which the composition is absorbed into the skin.

Treatment of Cold Sores using Exemplary Formulation

In one set of treatments, volunteers suffering from developing and/or developed cold sores (all patients were previously diagnosed as being infected with the Herpes simplex virus) applied topically a lip balm comprising 10.5 wt % tea polyphenols (or 12% POLYPHENON E) and 2 wt % of an essential oil mixture (Reunion geranium oil, lavender, tea tree, bergamot, chamomile, and eucalyptus oils) in a base of 50 wt % petrolatum, 15 wt % yellow beeswax, and 10 wt % lanolin. Particular application regimens are as described below, and amount of balm applied to the lips was generally equivalent to quantities applied for cosmetic purposes (e.g., amounts generally used for lip stick).

Patient A: Has a history of UV-induced outbreak of severe cold sores for several years, which typically presents as prodromal tingling, redness and tightening of the areas affected by the developing cold sores. The cold sore erupts as large ulcer within 24 hours of the prodromal symptoms and take up to three weeks, and more typically two weeks to heal completely. After topical application of the lip balm twice daily, eruptions, chapping, and sunburn of the lips were completely prevented after high UV exposure during a ski trip. This experience was repeated on three successive ski trips, with no cold sore developing previous five ski trips without lip balm resulted in cold sores on every one of five trips previously). Remarkably, after irregular application of the lip balm during another UV exposure, eruption of cold sores were prevented after application of the lip balm immediately following prodromal symptoms.

Patient B: 40-year-old with a history of cold sores five times per year covering a quarter of a lip for most of his adult life. Use of the lip balm reduced the incidence below two per year. Patient B applied the lip balm at the first prodromal symptoms, and then twice daily until the prodromal symptoms disappeared. Lip balm was also applied after eruption to treat the are affected with the cold sore. Patient B reported that the cold sores that do erupt are smaller, and are located more on the facial skin at the lip margin. Furthermore, cold sores appeared to heal significantly faster.

Patient C: a 9-year-old with a history of frequent cold sores lasting about 10-12 days. Application of the lip balm at the first sign of an outbreak shortened duration of lesions to about four days. Cold sores were significant smaller in size and less florid.

Thus, specific embodiments and applications of rapidly absorbing lipophilic skin compositions have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A topical hydrophobic composition for complete absorption into skin that comprises:
    a hydrophobic base, wherein the hydrophobic base is formulated from at least one of a saturated hydrocarbon, a paraffinic hydrocarbon, a wool fat, a triglyceride, a fatty acid, a silicon oil, and a wax and wherein the hydrophobic base is formulated as a cream, balm, or lipstick;
    wherein the hydrophobic composition has a total water content of equal or less than 5 wt %; and
    wherein the hydrophobic composition comprises in addition to the hydrophobic base an essential oil in an amount of between 0.5-15 wt %, wherein the essential oil has analgesic properties and is prepared from *Pelargonium graveolens*, and a green tea polyphenol extract at a concentration of at least 2 wt %; and
    wherein a concentration of the essential oil is effective to achieve substantially complete absorption of the entire hydrophobic formulation into the skin without leaving a greasy residue.

2. The topical formulation of claim 1 wherein the green tea polyphenol extract is present in an amount of at least 10 wt %.

3. The topical formulation of claim 2 further comprising ascorbic acid or a polyphenol stabilizing antioxidant in an amount that is at least 20% of an equimolar quantity of the green tea polyphenol extract.

4. The topical formulation of claim 1 further comprising a second essential oil, wherein the second essential oil enhances an analgesic effect of the formulation, and wherein the second essential oil has no analgesic effect.

5. The topical formulation of claim 4 wherein the enhancing of the analgesic effect is selected from the group consisting of an accelerated analgesic effect, a greater pain relief, an extended pain relief, and an improved palatability of the formulation.

6. The topical formulation of claim 4 wherein the second essential oil is selected from the group consisting of a bergamot oil, a eucalyptus oil, a lavender oil, a chamomile oil, and a melaleuca oil.

7. The topical formulation of claim 1 wherein the essential oil is prepared from *Pelargonium graveolens*, and wherein the formulation further comprises an antioxidant.

8. The topical formulation of claim 7 further comprising a second essential oil selected from the group consisting of a bergamot oil, a eucalyptus oil, a lavender oil, a chamomile oil, and a melaleuca oil.

9. The topical formulation of any one of claim 1 or claim 7 wherein the formulation comprises the green tea polyphenol extract in an amount that is effective to reduce a viral skin eruption on a lip.

10. The topical formulation of claim 9 wherein the viral skin eruption is precipitated by a herpes virus or a pox virus.

11. A topical composition that comprises a green tea extract in an amount of at least 2 wt % and an essential oil in an amount of between 0.5-15 wt %, wherein the essential oil is prepared from *Pelargonium graveolens*, the green tea extract and the essential oil being in admixture with a hydrophobic base, wherein the hydrophobic base is formulated from at least one of a saturated hydrocarbon, a paraffinic hydrocarbon, a wool fat, a triglyceride, a fatty acid, a silicon oil base and a wax base, wherein the green tea extract and the essential oil are present in the composition at a concentration effective to reduce or delay onset of a viral eruption on a skin, and wherein the topical composition has a total water content of equal or less than 5 wt %.

12. The topical composition of claim 11 wherein the total water content is equal or less than 1 wt %.

* * * * *